(12) United States Patent
Weidemann-Hendrickson et al.

(10) Patent No.: US 8,865,962 B2
(45) Date of Patent: Oct. 21, 2014

(54) MULTIPURPOSE MEDICAL WRAP

(76) Inventors: Linda A. Weidemann-Hendrickson, Two Harbors, MN (US); Fred M. Hendrickson, Two Harbors, MN (US)

( * ) Notice: Subject to any disclaimer, the term of this patent is extended or adjusted under 35 U.S.C. 154(b) by 247 days.

(21) Appl. No.: 13/290,698

(22) Filed: Nov. 7, 2011

(65) Prior Publication Data

US 2012/0123311 A1    May 17, 2012

Related U.S. Application Data (60) Provisional application No. 61/412,609, filed on Nov. 11, 2010.

(51) Int. Cl.
| | |
|---|---|
| A61F 13/00 | (2006.01) |
| A61F 13/12 | (2006.01) |
| A61F 13/10 | (2006.01) |
| A61F 13/64 | (2006.01) |

(52) U.S. Cl.
CPC .......... *A61F 13/64* (2013.01); *A61F 13/00021* (2013.01); *A61F 13/12* (2013.01); *A61F 13/10* (2013.01)
USPC ...................................... 602/53

(58) Field of Classification Search
USPC ......... 602/4, 5, 20, 23, 26, 27, 41, 53, 60–65, 602/75; 128/869, 876, 878, 882; D24/189–192; 607/112
See application file for complete search history.

(56) References Cited

U.S. PATENT DOCUMENTS

| | | | |
|---|---|---|---|
| 2,015,255 A * | 9/1935 | Charpier et al. ................. 602/61 |
| 2,868,193 A | 1/1959 | Kreft | |
| 2,957,475 A | 10/1960 | Drake | |
| 3,298,366 A * | 1/1967 | Moore et al. .................... 602/61 |
| 3,312,219 A * | 4/1967 | Peckham ........................ 602/65 |
| 3,695,258 A | 10/1972 | Castle | |
| 3,831,467 A * | 8/1974 | Moore ............................ 602/26 |
| 3,880,159 A | 4/1975 | Diamond | |
| 4,013,070 A * | 3/1977 | Harroff ........................... 602/21 |
| 4,215,687 A * | 8/1980 | Shaw .............................. 602/60 |
| D284,895 S | 7/1986 | Wirtz | |
| 4,870,956 A * | 10/1989 | Fatool et al. .................... 602/26 |
| 5,399,153 A * | 3/1995 | Caprio et al. ................... 602/26 |
| 5,653,244 A * | 8/1997 | Shaw ............................ 128/882 |
| 5,656,023 A * | 8/1997 | Caprio et al. ................... 602/63 |
| 5,681,271 A * | 10/1997 | Nelson ........................... 602/27 |
| 5,728,059 A * | 3/1998 | Wiesemann et al. ............ 602/64 |

(Continued)

FOREIGN PATENT DOCUMENTS

GB          1387801          3/1975

*Primary Examiner* — Patricia Bianco
*Assistant Examiner* — Raymond E Harris
(74) *Attorney, Agent, or Firm* — Richard C Litman (57) ABSTRACT

The multipurpose medical wrap serves as a dressing, covering, splint holder, and/or various other emergency medical uses. The wrap includes a central pad having two layers of material defining a plurality of internal pockets therebetween for the insertion of various treatment packs and/or splints therein. The pad includes a relatively soft sheet to protect the area to which it is applied, and a relatively thin, non-insulating sheet that allows the pad to be reversed for use in applying hot and cold packs and the like. An end flap extends from each end of the central pad for additional protection and/or treatment. A plurality of laterally overlapping straps extends from each side of the central pad. Corresponding opposite straps are interwoven to secure the wrap to the body, some straps being used to form a sling and/or torso securing swath when the wrap is used as an arm treatment.

4 Claims, 9 Drawing Sheets

(56) References Cited

U.S. PATENT DOCUMENTS

| | | | |
|---|---|---|---|
| 5,865,777 A * | 2/1999 | Detty | 602/26 |
| 5,906,206 A * | 5/1999 | Shaw et al. | 128/882 |
| 5,918,602 A * | 7/1999 | Shaw et al. | 128/882 |
| 6,099,489 A | 8/2000 | Herzberg et al. | |
| 6,109,267 A * | 8/2000 | Shaw et al. | 128/882 |
| 6,164,279 A | 12/2000 | Tweedle | |
| 6,338,723 B1 * | 1/2002 | Carpenter et al. | 602/75 |
| 6,464,658 B1 | 10/2002 | Darcey | |
| 6,617,485 B2 | 9/2003 | Herzberg | |
| 7,329,232 B2 * | 2/2008 | Lipshaw et al. | 602/61 |
| 7,867,185 B2 * | 1/2011 | Lipshaw | 602/75 |
| 2003/0055366 A1 | 3/2003 | Chalek | |
| 2005/0288614 A1 * | 12/2005 | Weatherly | 602/60 |
| 2006/0135898 A1 * | 6/2006 | Richardson | 602/19 |
| 2007/0043311 A1 | 2/2007 | Jaggan-Vince | |
| 2007/0282231 A1 | 12/2007 | Picard et al. | |
| 2007/0282232 A1 * | 12/2007 | Hoffman | 602/5 |
| 2008/0287849 A1 * | 11/2008 | Zukowski | 602/26 |
| 2012/0010551 A1 * | 1/2012 | Farrow et al. | 602/75 |

* cited by examiner

MULTIPURPOSE MEDICAL WRAP

CROSS-REFERENCE TO RELATED APPLICATION

This application claims the benefit of U.S. Provisional Patent Application Ser. No. 61/412,609, filed Nov. 11, 2010.

BACKGROUND OF THE INVENTION

1. Field of the Invention

The present invention relates generally to medical devices and equipment, and particularly to a multipurpose medical wrap for use as an emergency and/or first aid wrap, splint, bandage, dressing, or holder for various treatments for various areas of the body.

2. Description of the Related Art

First aid equipment and supplies are nearly universally provided in many environments and areas, ranging from schools, the workplace, and in the military and for many leisure activities as well. Moreover, hospitals and other emergency clinics will carry various emergency provisions as well, with such provisions intended for initial triage and temporary use until more permanent care can be given.

In many situations the provision of at least a moderate first aid kit is a legal requirement. First aid kits vary considerably in their completeness, but more advanced or complete kits will include materials and provision for dressing a serious wound, splinting a broken limb, protecting an injured body part, etc. The need to provide separate articles or supplies for each of these functions results in a first aid kit that is prohibitively bulky for many environments, e.g., for carriage on the person during military operations or hiking, or perhaps for carriage in a small car, boat, or aircraft.

Thus a multipurpose medical wrap solving the aforementioned problems is desired.

SUMMARY OF THE INVENTION

The multipurpose medical wrap serves as a dressing, covering, splint holder, and/or various other emergency medical treatment purposes. The wrap includes a central pad having two layers of material defining a series of internal pockets therebetween. Preferably a relatively large central pocket is provided for the placement of such treatments as hot or cold packs, relatively wide board splints, etc. therein. A relatively narrow sleeve extends along each of the opposite edges of the central pocket. The narrow outer sleeves provide for the insertion of elongate rigid articles therein to serve as splints.

One of the pad layers is a relatively thick, soft fabric material that serves to protect an injured area when placed adjacent thereto. The opposite layer or sheet is a relatively thin and optionally porous material that has little insulation value, but allows such devices as heat and cold packs to perform effectively when the thin, non-insulating layer is placed against the body.

An end flap extends from each end of the central pad. The end flaps may be used as additional insulation or padding, or as a pressure dressing when drawn up over a wound, e.g., an amputation. The end flaps may be tucked between the central pad and the body when not needed.

A plurality of laterally overlapping straps extends from each side of the central pad. These straps are used to secure the wrap to the body. Corresponding opposite straps are interwoven with one another to provide secure installation of the wrap to the body. Some of the straps at or toward opposite ends of the central pad may remain extended for use as a sling and/or torso securing strap or swath when the wrap is used as an arm sling or the like. A corresponding series of loops may be provided along both surfaces of each side or edge of the pad at the bases of the straps, to provide better security for the straps by passing them through the loops when securing the pad to the body.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The multipurpose medical wrap serves as a versatile emergency or first aid wrap, splint, bandage, dressing, and/or holder for various treatments for various areas of the body. The versatility of the wrap permits a single such wrap to be carried in a first aid kit or the like, thus greatly reducing the weight and bulk of such a kit that contains conventional special purpose supplies, each dedicated to a single function.

Figure 1:
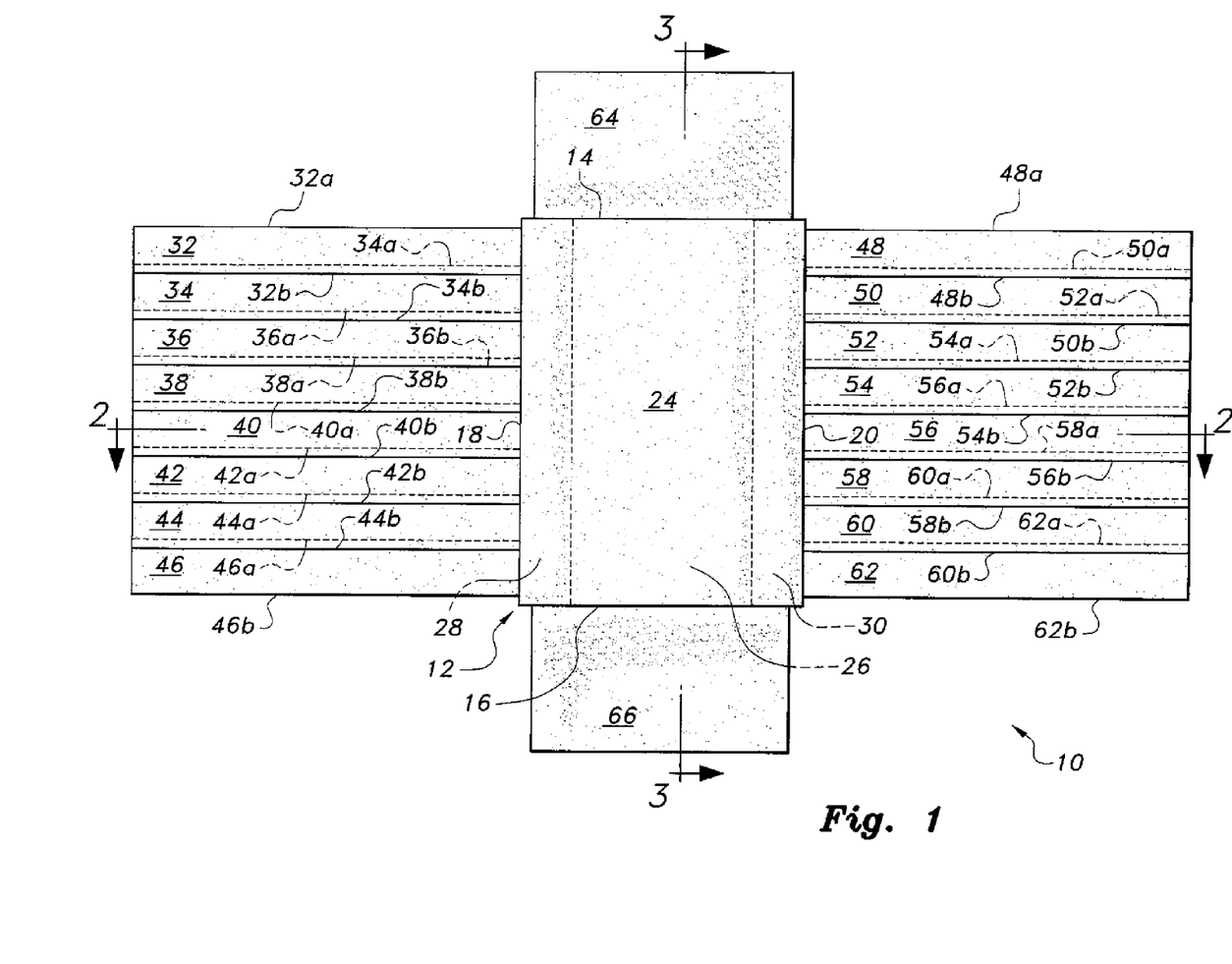
FIG. 1 is a top plan view of a multipurpose medical wrap according to the present invention, showing the wrap laid out flat to illustrate its components.
Figure 2:
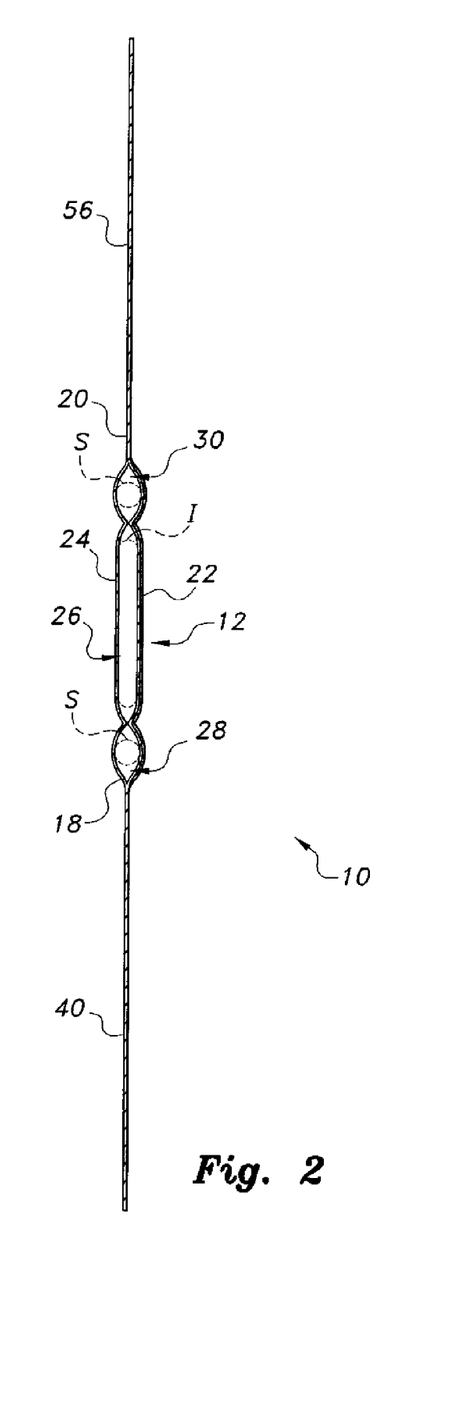
FIG. 2 is a section view along lines 2-2 of FIG. 1.
Figure 3:
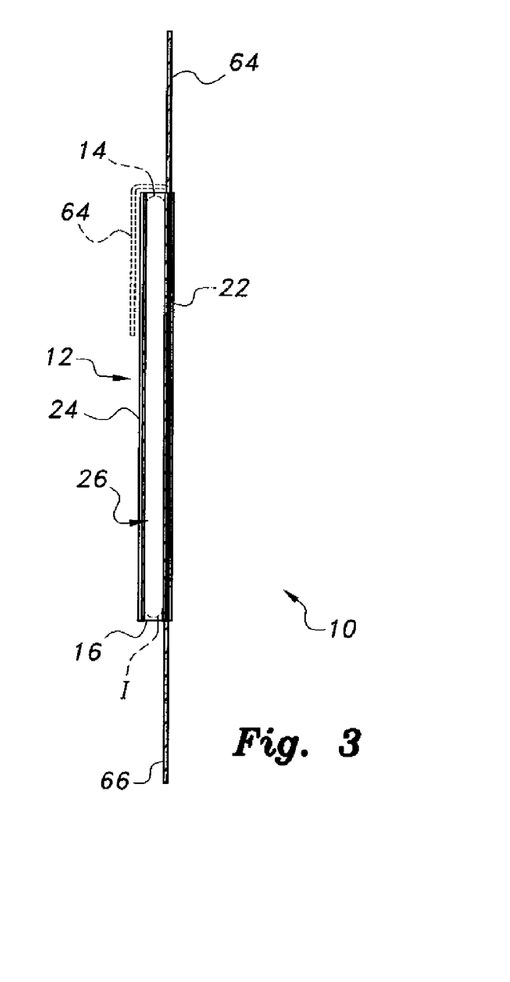
FIG. 3 is a section view along lines 3-3 of FIG. 1.

FIG. 1 of the drawings is a top plan view illustrating an exemplary multipurpose medical wrap, designated as wrap 10. The wrap 10 includes a central pad 12 having a first end 14, opposite second end 16, first lateral edge 18, and opposite second lateral edge 20. The pad 12 is formed of a first sheet of material 22 and a second sheet of material 24, shown most clearly in the section views of FIGS. 2 and 3. The two sheets 22 and 24 define a central pocket 26 and mutually opposed lateral first and second splint sleeves or passages 28 and 30 disposed adjacent and parallel to the first and second lateral edges 16 and 18 of the pad 12. It will be seen in FIGS. 1 and 2 that the two splint sleeves or passages 28 and 30 are considerably narrower than the central pocket 26, as the splint sleeves or passages 28, 30 are intended to hold relatively thin, stiff rods or the like to serve as splints for a broken limb. The central pocket 26 and lateral splint passages or sleeves 28, 30 are open for internal access thereto along at least one of the two opposite ends 14 and 16 of the pad 12.

The first sheet 22 comprises a thick, soft sheet of fabric material with good thermal insulation properties, while the opposite second sheet 24 comprises a thin, optionally porous ply of material with good thermal conductivity. This allows the pad 12 to be reversed to place either layer or sheet 22 or 24 against the body, depending upon the required treatment. For example, if treatment by a heat or cold compress is desired, the second sheet or layer 24 may be placed directly against the body, the appropriate hot or cold pack or compress placed within the central pocket 26, and the wrap 10 oriented to place the thermally conductive second sheet 24 against the body, thus optimizing thermal transfer from the compress or treatment to the body. Alternatively, the central pocket 26 may be used to contain some other device, such as a board-type splint, etc., such as the device generally indicated as insert I, shown in broken lines within the central pocket 26 in FIGS. 2 and 3 of the drawings. The two lateral splint passages or sleeves 28 and 30 are used to contain conventional rigid splints, the splints S being shown in broken lines in FIG. 2.

A plurality of first edge straps 32 through 46 (herein depicted as evenly numbered elements) extends from the first edge 18 of the central pad 12, and corresponding second edge straps 48 through 62 extend from the opposite second edge 20 of the pad 12. While the embodiment shown and described herein contains eight such lateral straps extending from each edge of the pad 12, it will be noted that more or fewer straps may be provided. Each of the straps has opposite first and second edges designated by the characters a and b in the drawings, e.g., the first lateral strap 32 extending from the first pad edge 18 has first and second lateral edges 32a and 32b, etc. The straps extending from each respective edge 18 and 20 overlap one another at least slightly, as shown in FIG. 1. The second edge 32b of the first strap 32 overlies the first edge 34a of the second strap 34, the second edge 34b of the second strap 34 overlies the first edge 36a of the third strap 36, etc. The second edge straps 48 through 62 (herein depicted as evenly numbered elements) have the same configuration. Thus, the overlapping straps form a continuous array of straps extending from each lateral edge 18, 20 of the central pad 12.

Mutually opposed first and second end flaps 64 and 66 extend from the first and second ends 14 and 16 of the central pad 12. Either or both of these end flaps 64 and 66 may be tucked between the body surface and the overlying pad 12, or may be extended beyond the pad 12 to provide additional coverage for the area being treated by the wrap 10. The first end flap 64 is shown in an alternative position in broken lines, folded over the top of the first sheet 24 of the central pad 12, in FIG. 3. All of the components of the wrap 10, i.e., the two sheets 22 and 24 comprising the central pad 12, its various edge straps 32 through 62, and the two end flaps 64 and 66, are preferably formed of natural and/or synthetic fabric materials that are transparent to X-ray radiation to allow the wrap 10 to remain in place during X-ray procedures. The above-noted components are devoid of metal fasteners and other metal components, and the splints S and insert I are preferably formed of non-metallic materials, e.g., wood or plastic in the case of the splints S. The fabric materials of which the various components of the wrap 10 are formed are preferably reusable after cleaning and sterilizing, and may be recyclable when the wrap 10 is no longer suitable for use.

Figure 4:
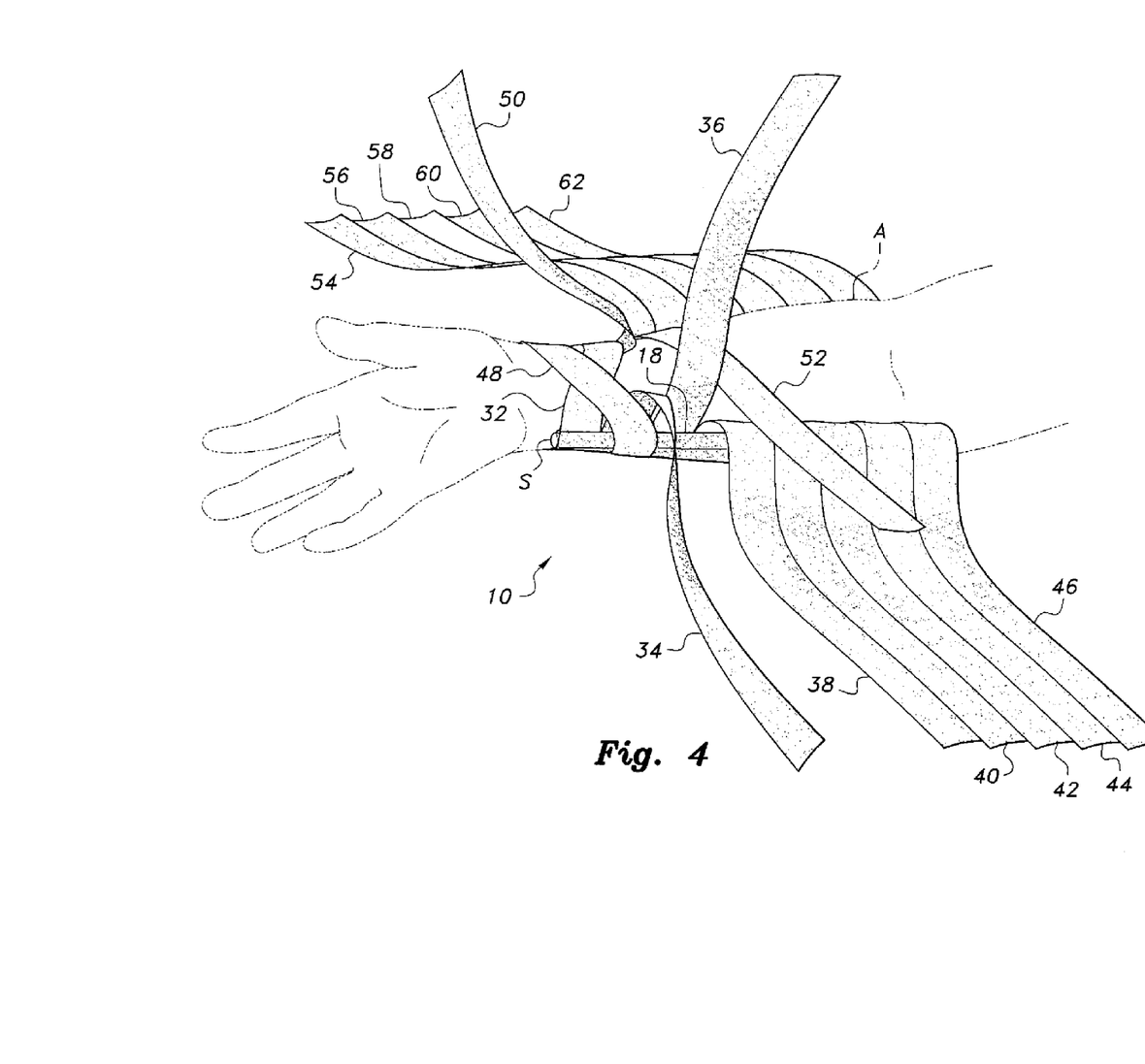
FIG. 4 is an environmental perspective view of an early stage in the application of the multipurpose medical wrap of FIGS. 1-3 to the right forearm of a person, showing the interweaving of the opposed lateral strips with one another.
Figure 5:
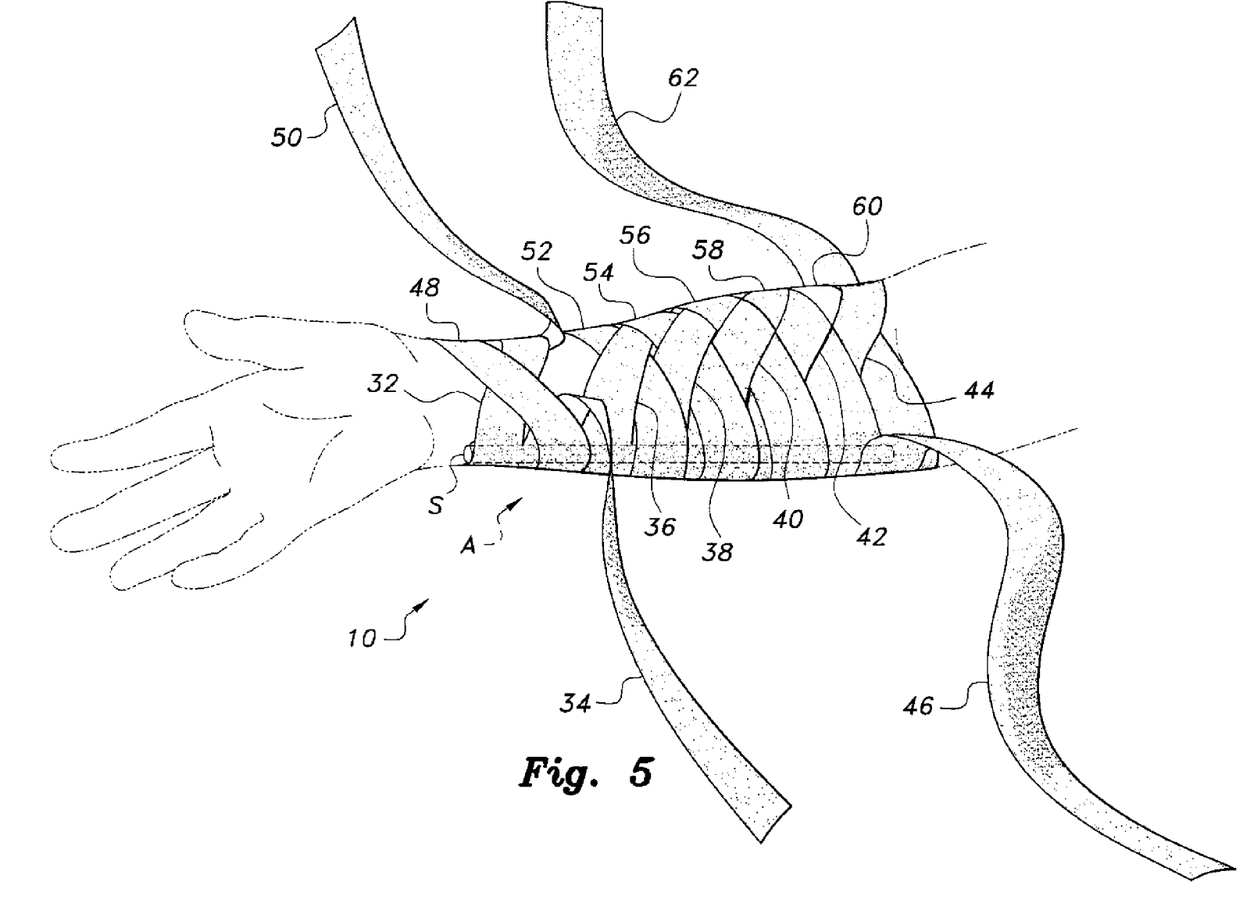
FIG. 5 is an environmental perspective view of the multipurpose medical wrap of FIG. 4 applied as a forearm splint, the strips remaining free for the formation of a support sling and a torso-retaining swath, if desired.
Figure 6:
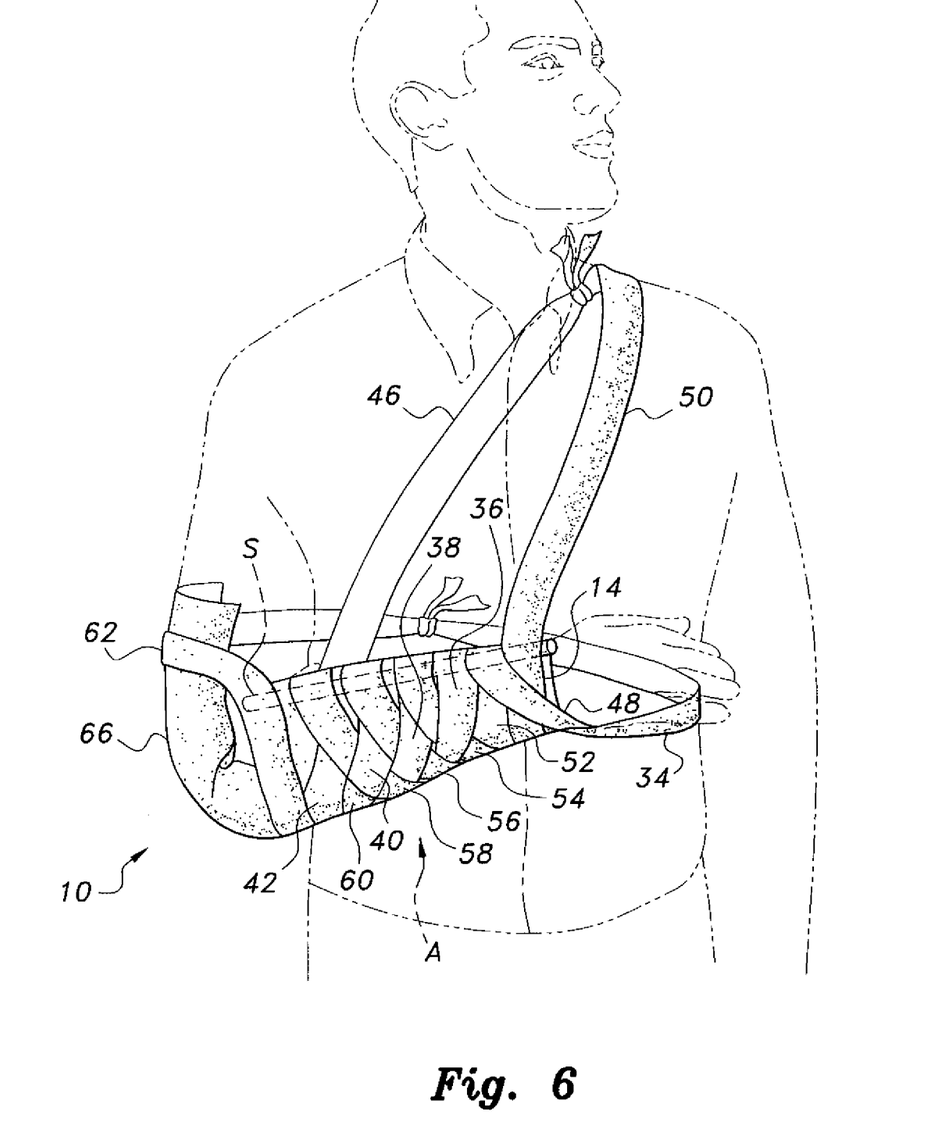
FIG. 6 is an environmental perspective view of the multipurpose medical wrap of FIGS. 4 and 5, showing the strips configured to provide an arm support sling and torso-retaining swath to secure the device about the body of the user.

FIGS. 4 through 6 illustrate an exemplary installation of the multipurpose medical wrap 10 for use in splinting and protecting a broken forearm A. FIG. 4 provides an illustration of an early portion of the procedure for installing the wrap 10. In FIG. 4, the pad 12 has been placed beneath the arm A, and the first and second splint sleeves or passages 28 and 30 are placed to either side thereof. A portion of the first edge 18 of the wrap is visible in FIG. 4. Initially, the forwardmost first and second edge straps 32 and 48, i.e., the straps closest to the first end 14 of the pad 12, are wrapped about the arm A and crossed diagonally about the arm. The next two straps, i.e., straps 34 and 50, remain free to be used to form portions of the arm support sling and swath (the band extending about the torso), as shown in FIG. 6 and discussed further below. The third straps away from the first end of the pad, i.e., straps 36 and 50, are shown extended to be wrapped about the forearm A in FIG. 4, the straps 36 and 50 crossing diagonally about the forearm A in the manner of the first two straps 32 and 48. The various straps 32 through 60, with the exception of the second and last straps on each side, are thus progressively interlaced or woven together from the wrist area toward the elbow to secure the wrap 10 about the forearm A.

FIG. 5 illustrates the final wrap configuration with the two sling straps 46 and 50 and the two swath straps 34 and 62 remaining free. It will be seen in FIG. 5 that the other straps 32, 36 through 44, 48, and 52 through 60, are interwoven with one another to provide a secure installation for the wrap 10 upon the forearm A. Any loose strap ends remaining may be tucked beneath other straps for security.

FIG. 6 illustrates an exemplary completed placement of the wrap 10 upon the forearm A. The orientation of the view in FIG. 6 has been turned approximately 180° from that shown in FIGS. 4 and 5, so that the first end 14 of the pad 12 is to the right. In FIG. 6, the second of the straps extending from the second edge, i.e., strap 50, has been extended upward to pass over the shoulder of the patient, and the last of the first edge straps, i.e., strap 46, passes diagonally upward and across the back of the patient, where the two straps 46 and 50 are tied together to complete the sling portion of the arm support. The second strap extending from the first edge of the pad, i.e., strap 34, is passed generally horizontally about the torso of the patient and connected to the last of the straps extending from the second edge of the pad, i.e., strap 62, to form the swath portion of the arm support. The specific straps used to form the sling and swath may be adjusted as desired, but it has been found that the use of the second strap 34 and 50 extending from each pad edge works well in supporting the arm, while the first two straps 32 and 48 provide better distal support near the wrist in similar manner. The second end flap 66 has been extended about the elbow to provide further protection, support, and comfort, the last strap 62 extending from the second side of the pad 12 wrapping about the second end flap 66 to hold it in position.

Figure 7:
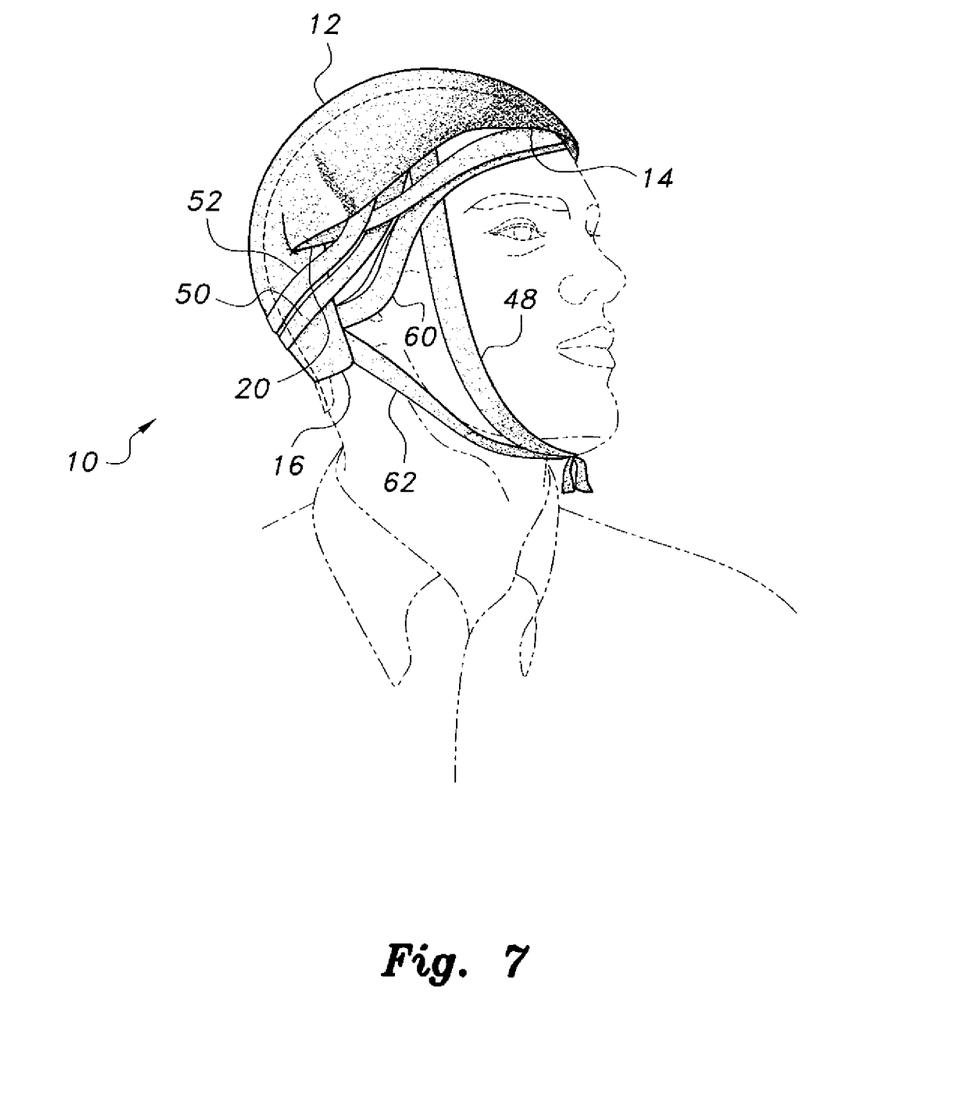
FIG. 7 is an environmental perspective view of the multipurpose medical wrap of FIGS. 1-3 configured as a dressing or wrap for the head of a person.

FIG. 7 of the drawings illustrates an exemplary application of the multipurpose medical wrap 10 for use in treating a head wound or injury. In FIG. 6, two strap pairs have been extended from the central pad 12 for use as ties beneath the chin of the patient, and other strap pairs pass about the forehead and over the back of the pad 12 for further security. In the example of FIG. 6, the foremost strap 48 and the rearmost strap extend generally downward to secure to their counterpart straps (not shown) extending from the left side, where they are secured to one another beneath the chin. Another second side strap 60 is seen extending forwardly to pass around the forehead of the patient. Still other second side straps 50 and 52 extend rearward to pass over the outside of the back of the central pad 12 to secure it closely to the patient's head. Obviously, any splints or other rigid material is omitted from such an installation in order to provide the required flexibility about the body structure. It will be understood that each of the straps shown in FIG. 7 is attached (e.g., tied, etc. to its counterpart extending from the concealed opposite first side of the pad 12. Other straps not used may be tucked between the pad 12 and the head to provide greater absorption, insulation, retention of medication, and/or other function(s).

Figure 8:
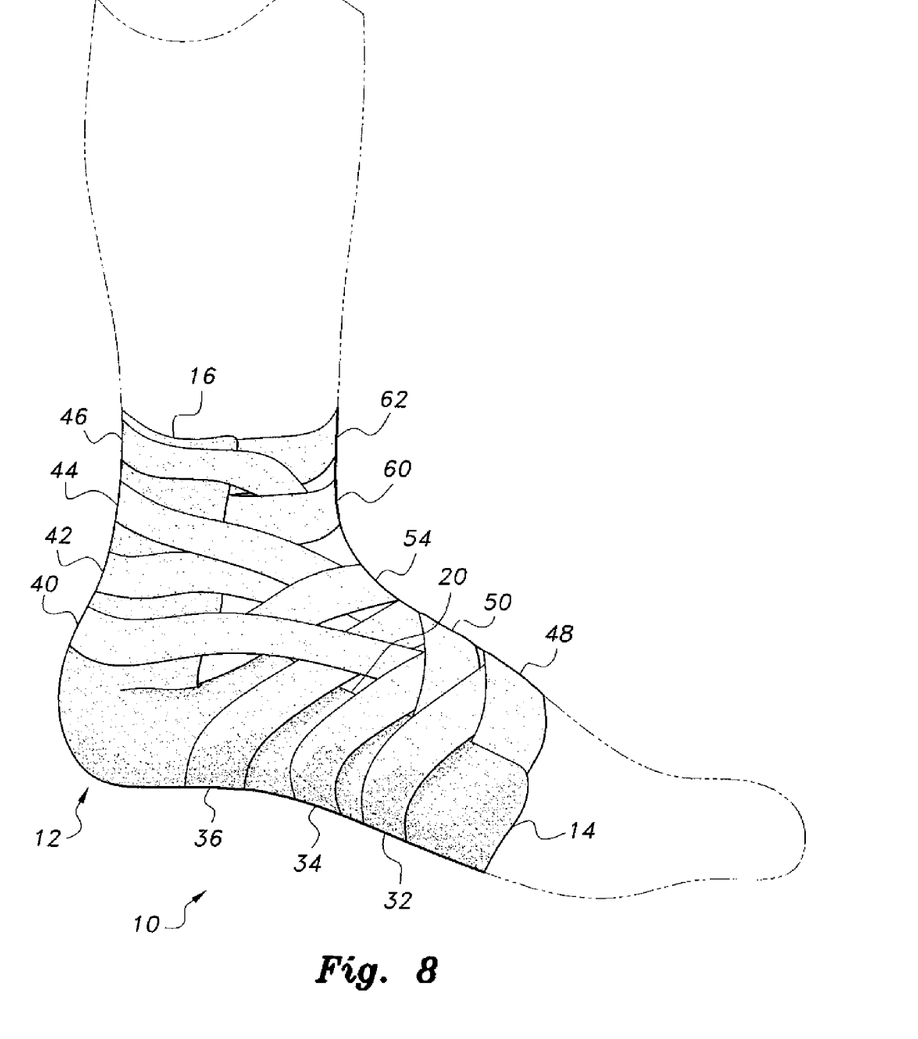
FIG. 8 is an environmental perspective view of the multipurpose medical wrap of FIGS. 1-3 configured for installation upon the foot and ankle of a person.

FIG. 8 illustrates an exemplary application of the multipurpose medical wrap to a foot. In FIG. 7, the central pad 12 has been placed beneath the foot to extend about the heel and at least partially up the back of the ankle, the first end 14 being positioned beneath the area of the forward portion of the arch or below or slightly behind the ball of the foot. The opposite second end 16 of the pad 12 is wrapped about the back of the upper ankle. It will be understood that this exemplary placement of the pad 12 may be adjusted as required, and that any rigid splints or the like are omitted, as in the case of the head treatment illustrated in FIG. 6. The various straps are again interlaced or interwoven with one another from the opposite sides or edges of the pad 12, as in the examples provided further above. It will be noted in FIG. 7 that some of the straps are not shown. Some such straps may be tucked between the foot and the pad 12, as there may be insufficient area about the arc defined by the top of the foot and the front of the ankle or shin to allow all of the straps to be used without undue interference or bulk. The specific arrangement of the straps may be devised by the person applying the wrap 10, so long as an appropriate interweaving or interlacing of straps from opposite sides of the pad is used for security of installation.

Figure 9:
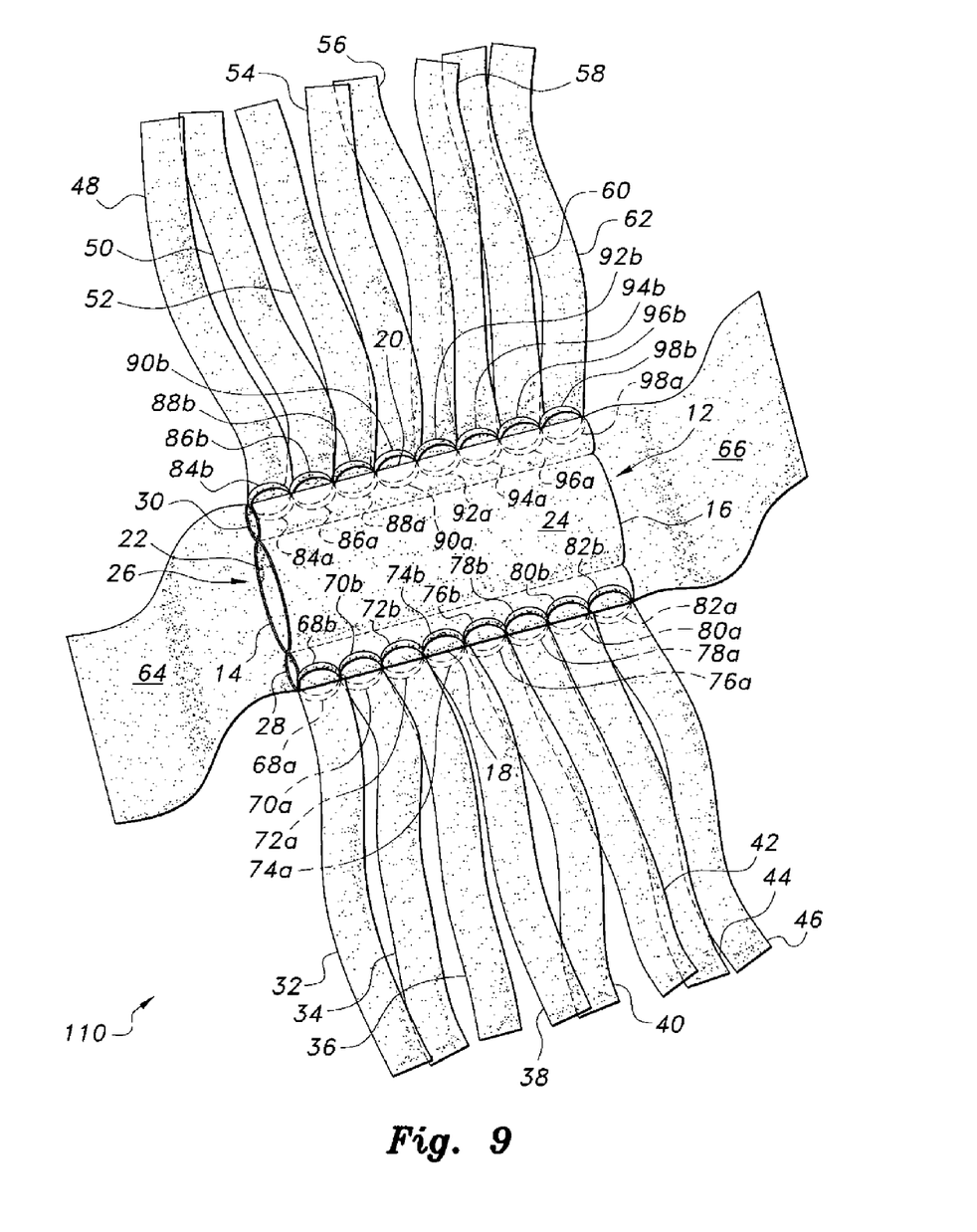
FIG. 9 is a perspective view of an alternative embodiment of a multipurpose medical wrap according to the present invention, showing a plurality of strap securing loops along the opposed strap attachment edges of the pad.
Figure 10:
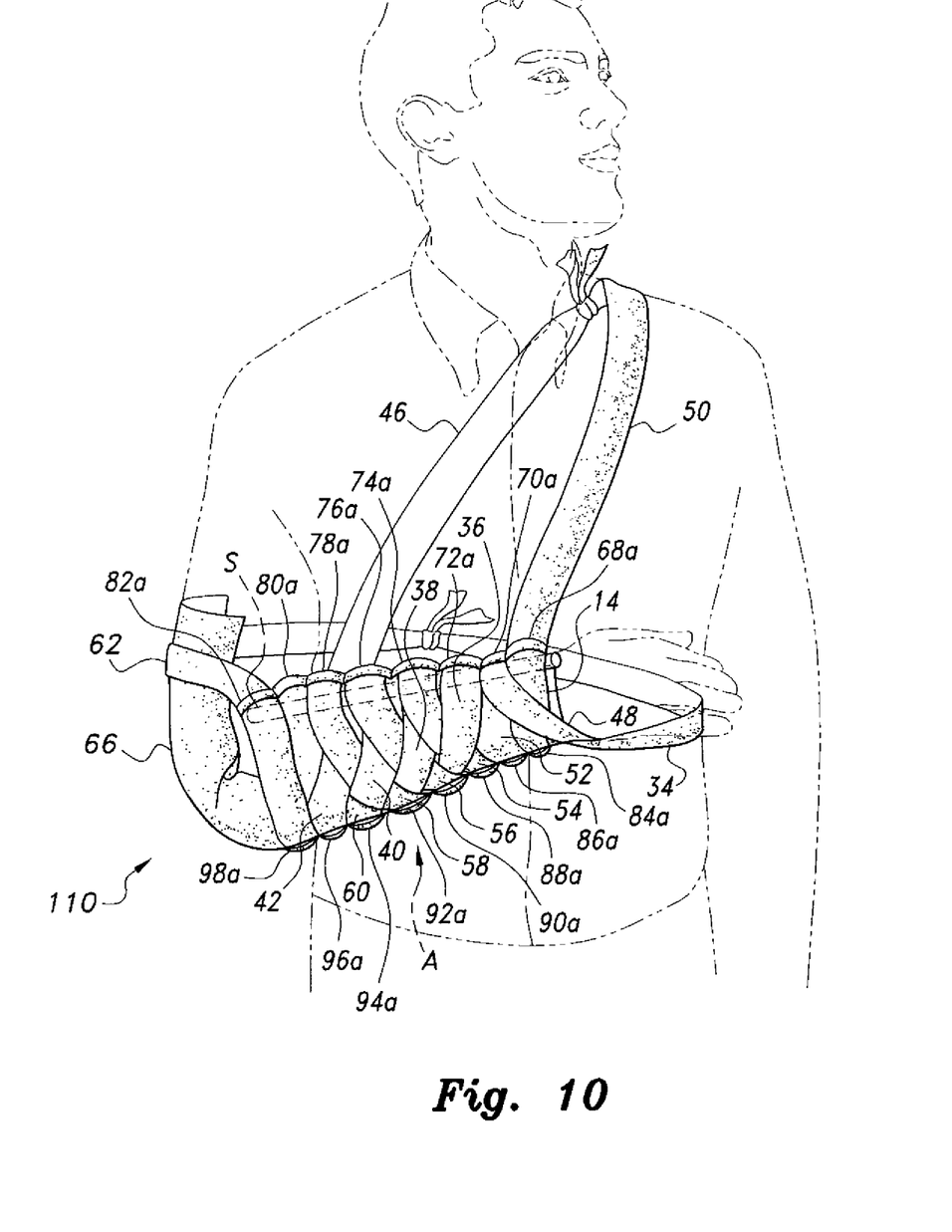
FIG. 10 is an environmental perspective view of the multipurpose medical wrap of FIG. 9, showing the wrap configured to provide an arm support sling and torso-retaining swath similar to the configuration of FIG. 6, but with the straps secured by the strap retaining loops.

FIGS. 9 and 10 of the drawings illustrate a slightly different embodiment of the multipurpose medical wrap, designated as multipurpose medical wrap 110. The wrap 110 includes all of the components of the wrap 10. Those like components of the wrap 110 that are shown in FIGS. 9 and 10 are indicated by the same reference numerals as used to indicate those components of the wrap 10 shown in previous drawings. However, the wrap 110 further includes a plurality of strap retaining loops disposed along the opposite first and second edges 18 and 20 of the central pad 12, where the straps 32 through 62 join their respective attachment edges 18 and 20.

FIG. 9 illustrates four sets of loops along the pad edges. The first loop set comprises loops 68a through 82a extending along the first edge 18 of the first sheet 22 of the pad 12. This first loop series 68a through 82a is shown in broken lines in FIG. 9, as the first sheet 22 is beneath the second sheet 24 due to the orientation in this drawing. An opposite set of loops 68b through 82b is installed along the first edge 18 of the opposite first sheet 24. Corresponding loop sets 84a through 98a and 84b through 98b are installed along the respective second edge 20 of the first and second sheets 22 and 24. Each of the four loop sets, e.g., loop series 68b through 82b, may be formed of a single continuous band of material that is stitched or otherwise secured to the underlying edge of the sheet by a series of spaced apart lateral attachments to provide a number of loops along the band to correspond with the number of straps extending from that edge. Alternatively, the loops may be individually formed and attached, if desired.

The provision of four sets of loops allows the multipurpose medical wrap 110 to be used in any practicable orientation. Either of the sheets 22 or 24 is placed against the body surface, and the opposite sheet is disposed outwardly. Moreover, the straps extending from both edges may be secured by corresponding loops along the opposite edge in this manner. However, it will be seen that fewer than the four sets of loops may be provided, if desired, e.g., only a single set along one edge of one sheet, or two sets along the common edge of the two sheets 22 and 24, or perhaps two opposed loop sets along opposite edges 18 and 20 of a single sheet.

FIG. 10 provides an illustration similar to FIG. 6, but showing the multipurpose medical wrap embodiment 110 placed upon the forearm A. The orientation of the multipurpose medical wrap 110 shown in FIG. 10 is the same as the orientation of the wrap 10 shown in FIG. 6, i.e., the first end 14 of the pad 12 is to the right. The strap configuration is also the same in FIG. 10 as in FIG. 6, with straps 46 and 50 forming the sling and straps 34 and 62 secured around the trunk of the subject to form a securing swath.

The various straps of the multipurpose medical wrap 110 of FIG. 6 are passed through the corresponding loops extending from the central pad 12 of the wrap 110 to provide better positional security for those straps, and to prevent them from slipping longitudinally along the applied wrap 110. Only loops 68a through 98a are visible in FIG. 10 due to the orientation of the installed wrap 110 on the forearm A of the subject.

It will be seen that the strap 50 used to form a part of the sling extends from the lower portion of the assembly to pass through the opposite loop 68a. Similarly, strap 54 wraps around the outside of the installed wrap 110 to pass through the loop 74a, and strap 58 passes through the loop 80a and the strap 62 that is used to form a part of the swath of the installed wrap 110 passing through the loop 82a. Certain of the opposite edge straps are passed through corresponding loops to their opposite edge. It will be understood that not all straps can be inserted to pass through various loops, as approximately half of the straps will pass beneath other straps, while the corresponding loops are positioned outside of those other straps. However, the installation of at least some of the straps through appropriate loops, as described, greatly increases the security of the straps around the installed wrap 110 and prevents those straps from slipping longitudinally along the installed wrap.

The multipurpose medical wraps 10 and 110 are not limited to use only as illustrated in the drawings, but may be used to treat virtually any part of the body, e.g., upper or lower leg, torso (the straps may be made sufficiently long for securing about the torso), hand, etc. Also, while the use of the wraps 10 or 110 as a splint in securing a broken limb is illustrated in FIGS. 4 through 6 of the drawings, it should be noted that the wraps 10 and 110 may be used as a compress or to hold an ointment or other treatment closely against the wound or injury in lieu of or in addition to its use as a splint. The end flaps 64, 66 are useful in providing additional padding for an injury, and/or they may be useful in protecting the stump of an amputation or in a case where a portion of a limb was removed traumatically in the field, as might occur in a serious auto accident or in combat. While other means of securing the sling and swath straps or bands of the wrap to one another may be used, it has been found that tying the sling and swath straps to one another works well in the field, as such attachment is very quick and requires no additional clamps, clips or other components. Thus, the present multipurpose medical wrap is well suited for use in an emergency or first aid kit, where its versatility may prove to be extremely valuable when needed.

It is to be understood that the present invention is not limited to the embodiments described above, but encompasses any and all embodiments within the scope of the following claims.

We claim:

1. A multipurpose medical wrap, comprising:

a pad having a first end, a second end opposite the first end, and mutually opposed first and second lateral edges, the pad being formed from a first sheet of material and a second sheet of material, the first sheet of material of the pad is formed from thick soft fabric having thermal insulation properties, the second sheet of material is formed from a thin porous ply having thermal conductivity properties, the first and second sheets of material defining a central pocket therebetween extending from the first end to the second end of the pad and first and second splint sleeves extending from the first end to the second end of the pad, the central pocket being larger than each of the first and second splint sleeves, the splint sleeves being adjacent, parallel and contiguous to the respective lateral edges of the pad, the central pocket and each of the splint sleeves having at least one continuously open end;

a plurality of first edge straps extending outwardly from the first lateral edge of the pad, wherein each of the first edge straps has at least one edge overlapping at least one edge of another of the first edge straps, all of the first edge straps being joined to the first lateral edge of the pad in a continuous array; and a plurality of second edge straps extending outwardly from the second lateral edge of the pad, wherein each of the second edge straps has at least one edge overlapping at least one edge of another of the second edge straps, all of the second edge straps being joined to the second lateral edge of the pad in a continuous array.

2. The multipurpose medical wrap according to claim 1, further including:

a first end flap extending from the first end of the pad; and a second end flap extending from the second end of the pad.

3. The multipurpose medical wrap according to claim 2 wherein:

the pad, the first edge straps, the second edge straps, the first end flap, and the second end flap are devoid of metal and substantially transparent to x-ray radiation; and the pad, the first edge straps, the second edge straps, the first end flap, and the second end flap are constructed of reusable and recyclable material.

4. The multipurpose medical wrap according to claim 1, further comprising a plurality of strap-retaining loops disposed along at least one lateral edge of at least one sheet of material of the pad.

* * * * *